United States Patent [19]
Kilmartin

[11] 4,307,724
[45] Dec. 29, 1981

[54] OBSTETRIC DEVICE FOR ASSISTING IN THE BIRTH OF ANIMALS

[76] Inventor: Vincent J. Kilmartin, "Sol Vista", Kinnegad, County Westmeath, Ireland

[21] Appl. No.: 125,038

[22] Filed: Feb. 27, 1980

Related U.S. Application Data

[63] Continuation-in-part of Ser. No. 902,229, May 2, 1978, abandoned.

[51] Int. Cl.³ .............................................. A61B 17/42
[52] U.S. Cl. ..................................................... 128/352
[58] Field of Search ........................ 128/352, 353, 324

[56] References Cited

U.S. PATENT DOCUMENTS

| | | | |
|---|---|---|---|
| 745,992 | 12/1903 | Bargeboer | 128/352 |
| 1,885,945 | 11/1932 | Ransy | 128/352 |
| 2,692,600 | 10/1954 | Curyea | 128/352 |
| 2,703,578 | 3/1955 | Horst | 128/352 |
| 3,643,664 | 2/1972 | McMillan | 128/353 |
| 3,955,582 | 5/1976 | Pierce | 128/352 |

FOREIGN PATENT DOCUMENTS

| | | | |
|---|---|---|---|
| 260572 | 6/1913 | Fed. Rep. of Germany | 128/352 |
| 2214012 | 10/1973 | Fed. Rep. of Germany | 128/352 |
| 634942 | 12/1927 | France | 128/352 |
| 609159 | 9/1960 | Italy | 128/352 |

*Primary Examiner*—Dalton L. Truluck
*Attorney, Agent, or Firm*—Young & Thompson

[57] ABSTRACT

An obstetric device for assisting in the birth of animals, has an end frame that abuts the pelvis of the dam and defines an aperture through which the offspring is delivered, and a longitudinal frame member that extends perpendicularly away from the end frame member and is connected thereto by a U-shaped portion that lies in a plane perpendicular to the end frame. The legs of the U-shaped portion are secured to opposite side portions of the end frame at positions on the side portions below their midpoints but above their lower ends so that the greater part, but not all, of the delivery aperture is positioned above the longitudinal frame member. At the other end of the longitudinal frame member, a T-shaped portion provides axles for winding drums that are freely rotatable in either direction thereon, independently of each other. A delivery rope is wound up on each drum, for attachment to the forelegs of the offspring. Handles are provided on the winding drums to rotate them manually so as to tension the delivery ropes.

2 Claims, 8 Drawing Figures

OBSTETRIC DEVICE FOR ASSISTING IN THE BIRTH OF ANIMALS

This application is a continuation-in-part of my co-pending application Ser. No. 902,229, filed May 2, 1978 and now abandoned.

This invention relates to an obstetric device for use in assisting in the birth of animals, in particular for assisting in the birth of calves and foals.

It is frequently necessary to assist an animal in giving birth to its young by pulling on the forelegs of the nascent offspring. This is particularly so in the case of cattle where either the mother is debilitated or the calf is exceptionally large. A number of birth-assisting devices are known. For example, British patent specifications Nos. 916,239 and 1,434,994 describe an obstetric device for livestock comprising a support member which is placed against the body of the mother, and having a tube connected thereto. Leg slings are attached to the forelegs of the calf being delivered and the ends of the slings are attached to hooks which are mechanically displaced along the tubes by a tension lever to alternately tension the slings. One disadvantage of using a rachet mechanism, such as described in the aforesaid specifications, for pulling the slings is that the tension in the slings cannot be readily varied at will and the operator is unable to sense the tension being exerted on the calf, and as a result injury may be caused to the cow or calf. Obstetric apparatus in which there is a minimum interference with the operator's tactile sense is described in British patent specification No. 902,698. This appliance comprises a framework having an abutment at one end of the frame portion which seats against the rear of the cow and which is shaped to permit passage of the calf therethrough, and a single crank and axle at the other end of the frame to apply tension to a delivery sling. The disadvantage of this appliance is that it is not possible to apply separate tension through the slings to each of the forelegs of the calf, which is usually necessary in the early stages of calving in order to ease one foreleg in front of the other. Furthermore, the particular construction of the framework described in British patent specification No. 902,698 would tend to obstruct the delivery of the calf.

It is an object of the present invention to overcome the aforesaid disadvantages and to provide a simple obstetric device for assisting in the birth of animals in which tension can be applied independently to each of the forelegs of the offspring being delivered which does not interfere with the operator's tactile sense and which causes a minimum of pain or discomfort to the dam or offspring.

According to the invention an obstetric device for assisting in the birth of animals comprises:

(a) an end frame to which is attached at least one longitudinal frame member extending rearwardly and perpendicularly away from the end frame, and in which the frame has a top portion, a bottom portion and two side portions which define an aperture through which the nascent offspring may be delivered, abutment members connected to each side portion and converging rearwardly of said end frame in the general direction of the longitudinal frame member, whereby when the device is in use the end frame is adapted to abut the pelvis of the dam with the top frame portion positioned above the tail of the dam, while at least a portion of each abutment member is adapted to engage with the ischial tuberosities of the dam, and the bottom portion of the frame is adapted to press against the legs of the dam, (b) a pair of winding drums rotatably mounted on an axle or axles located at the end of the longitudinal frame remote from the end frame and which extend transversely of said longitudinal frame in a plane parallel to the plane of the end frame, and each winding drum being rotatable independently of the other, (c) a delivery rope attached by one end to, and adapted for winding up on each of said winding drums the other end of each delivery rope being provided with means for attaching the rope to the forelegs of the nascent offspring, and (d) a handle located at each outer side of, and spaced from, the longitudinal frame member and connected to each winding drum, by means of which each drum can be manually rotated independently of the other to apply separate tension to each delivery rope.

Some embodiments of the invention are hereinafter described with reference to the accompanying drawings wherein.

Figure 1:
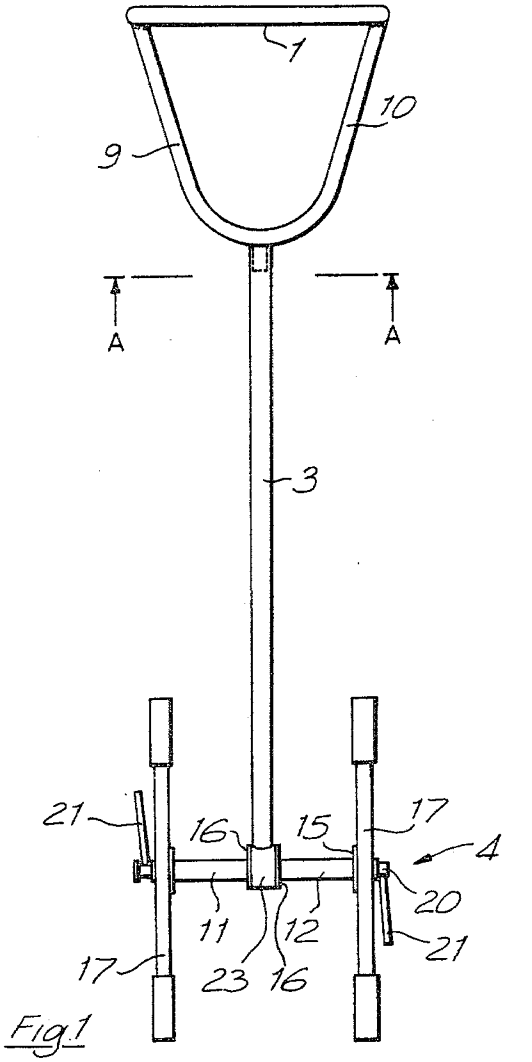
FIG. 1 is a plan view of one embodiment of obstetric device according to the invention.
Figure 2:
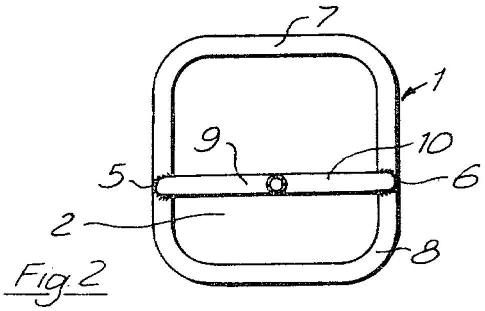
FIG. 2 is an elevation in the direction of the arrows A of FIG. 1.
Figure 3:
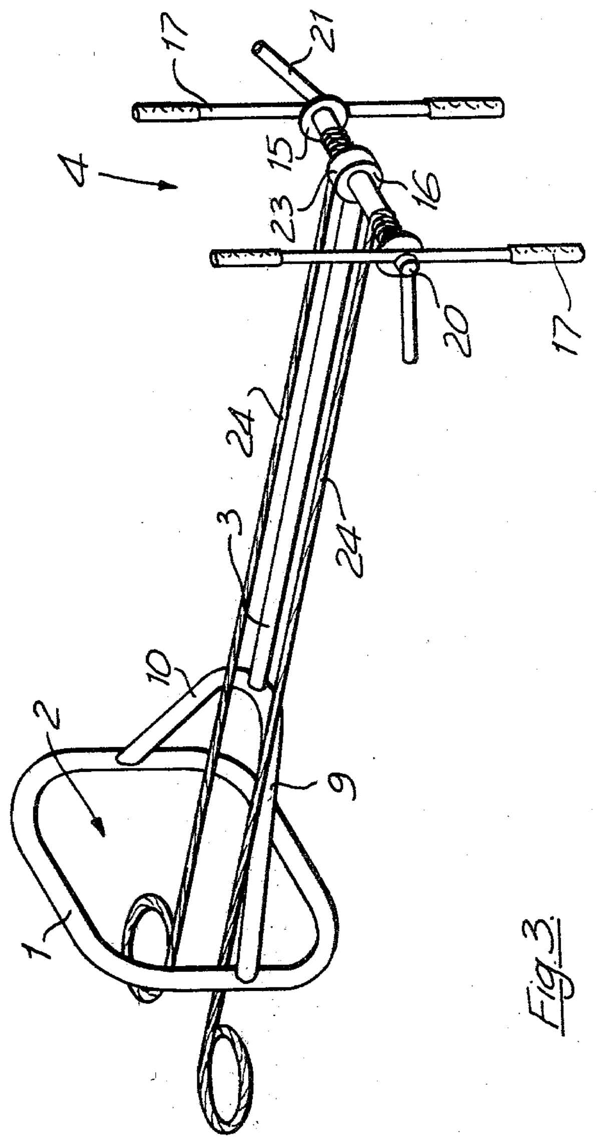
FIG. 3 is a perspective view of the device of FIG. 1.

Referring to FIGS. 1 to 4 of the drawings, an obstetric device for use in assisting in the birth of animals comprises an end frame 1 which defines a delivery aperture 2. The end frame 1 is connected by a longitudinal frame member 3 to traction means 4. The end frame 1 is of substantially square shape having curved corners and is comprised of two side portions 5, 6, a top portion 7 and a bottom portion 8. The longitudinal frame member 3 is substantially Y-shaped, and the shorter limbs 9, 10 of the member are rigidly attached to the side portions 5, 6 respectively of the end frame 1, at positions on the side portions 5, 6 below their mid-points. Thus, when the device is held horizontally, the greater part of the delivery aperture 2 is positioned above the longitudinal frame member 3. This ensures minimum obstruction of the delivery aperture.

Figure 4:
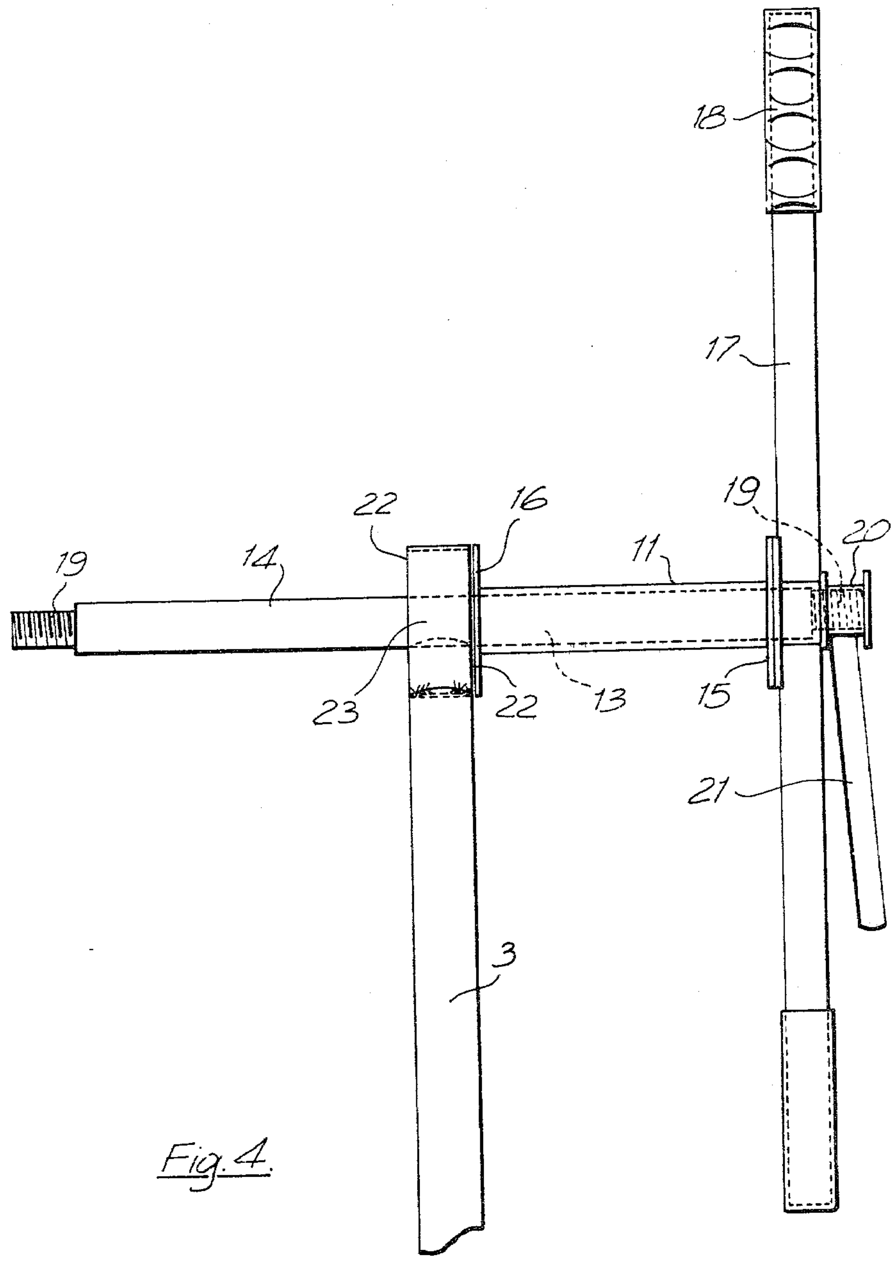
FIG. 4 is a detailed view of the winding drums and the device of FIG. 1.

The traction means 4 is shown in greater detail in FIG. 4. The longitudinal frame member 3, at the end remote from the end frame 1 is T-shaped and tubular drums 11, 12 are rotatably mounted on the short arms 13, 14 respectively of the T which act as axles. For the sake of clarity only one of the drums is shown in position in FIG. 4, the other being removed to show the axle 14. Each of the drums 11, 12 is provided with annular flanges 15, 16 at each end thereof. Each flange 15 is welded or otherwise secured to a handle 17 by means of which each drum 11, 12 may be manually rotated on its respective axle. The ends of each handle 17 is preferably provided with a rubber grip 18.

The outer ends 19 of the axles 13, 14 are screw-threaded to each receive a locking nut 20 which is provided with a suitable handle 21. Rotation of the locking nut forces the face of the flange 16 against an annular bearing face 22 on a collar 23 welded to the end of the longitudinal frame member 3, thus retarding or preventing rotation of the drum 11, 12.

Figure 7:
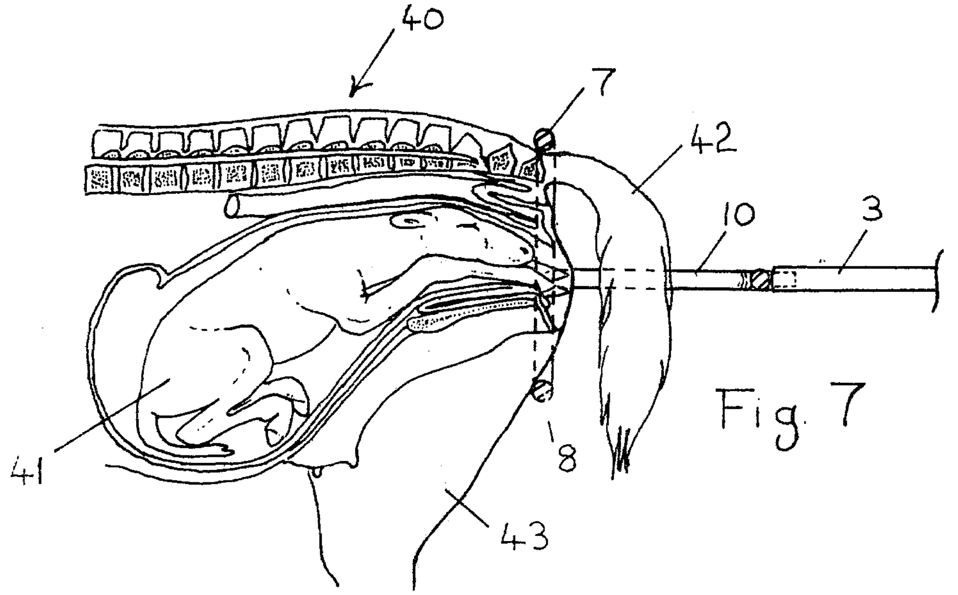
FIGS. 7 and 8 are illustrations of the use of the device of FIG. 1 to assist in the birth of a foal.
Figure 8:
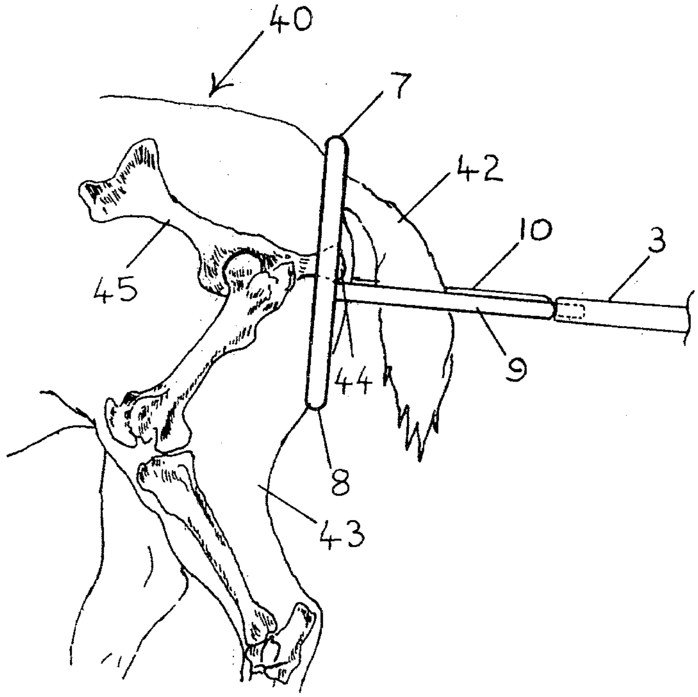

The method of using the device of the invention is illustrated in FIGS. 7 and 8. These Figures illustrate the device being applied to a mare 40 giving birth to a foal 41 but the device is used in exactly the same way with a cow giving birth to a calf. The relevant bone structure and vaginal area of a mare is similar to that of a cow. At partuition the vaginal area of the dam becomes enlarged, soft and oedematous, and the pelvic ligaments become lax to facilitate passage of the offspring. These tissues are easily damaged by bruising and so the correct positioning of obstetric devices on the dam is important. Furthermore, if the device is badly designed or incorrectly used there is a danger that the offspring's foot may pierce the vaginal wall, or that the perineum becomes torn which would have fatal consequences. Thus obstetric devices of the kind in which the end frame is designed to fit immediately beneath the tail against the aforesaid sensitive tissues can cause suffering to the dam and may lead to birth complications.

As illustrated in FIGS. 7 and 8, the device of the invention is so designed that when the end frame 1 is placed against the pelvis of the dam, the top frame portion 7 fits above the tail 42 of the dam 40 while the bottom frame portion 8 presses against the back of the dam's legs 43. The pressure of the bottom frame portion tends to urge the legs forward which assists in arching the dam's back and straightening the inlet to the vaginal canal. The limbs 9, 10 forming the U-shaped portion of the longitudinal frame form abutment members which anchor on the ischial tuberosities 44 of the dam. The ischial tuberosities consist of a pair of bones which form rearward extensions of the pelvis 45. The ischial tuberosities 44 protrude rearwardly at the tail end of the dam and one is positioned to each side of the vaginal opening. Because the abutment members 9, 10 converge rearwardly they are adapted to anchor below and against the ischial tuberosities of a wide variety of sizes of dam it being appreciated that the spacing apart of the ischial tuberosities can vary depending on the size of the dam. The abutment members 9, 10 thus form a cradle into which the ischial tuberosities fit. The ischial tuberosities form the strongest part of the pelvis and the provision of the abutment members 9, 10 enables the operator to anchor the device against this strong bone structure without fear of damage to the dam. This is not possible with known calfing aids which frequently are adapted to abut the pelvic area immediately below the tail of the dam and so may interfere with the natural contractions of the dam because pressure is being applied too near the vulvus and is in danger of damaging the perineum. The device of the invention when applied to the dam as described can be moved to the left or to the right to ease the offspring through the pelvic girdle, and because the abutment member can lever on the ischial tuberosities the longitudinal frame member may be moved downwards towards the dam's hocks so that the offspring can be pulled straight at first and then in a semi-circle. The abutment members 9, 10, because they are adapted to anchor against the ischial tuberosities, prevent the top frame portion from slipping which could cause injury to the spinal cord and tail of the dam.

Although the abutment members 9, 10 converge rearwardly to form a substantially U-shape or Y-shape cradle, it will be appreciated that the abutment members could comprise a substantially straight bar extending transversely of the end frame but which lies in a plane rearwardly of and substantially parallel to the plane of the end frame.

The dam may be standing or sitting during delivery of the offspring and the device may be used in either position. In a normal delivery the offspring emerges through the pelvic opening in a dorsal position as shown in FIG. 7, that is with the two forelegs stretched out in front with the head and neck extended on top of them. A delivery rope 24 (see FIG. 3) is looped on to each of the forelegs of the offspring and the ropes are brought back through the delivery opening 2 of the end frame 1 and the end of each rope is secured to a hook or spigot (not shown) on a respective winding drum 12, 13. The ropes are wound up on their respective winding drums, by turning the handle 17, to apply tension on the offspring's legs. The tension in the ropes causes the end frame 1 to abut firmly against the dam's pelvic girdle. As delivery commences each leg is pulled alternately as the dam strains, by rotating the respective winding drum, so that one of the forelegs of the offspring emerges in front of each other. Normally, the head will move with the forelegs but in some cases the head may lag behind and one or other of the delivery ropes 24 may have to the slackened so that the offspring's head is brought into the correct position. In other cases one or both of the forelegs may be bent backwards causing an obstruction; and these will require to be straightened and then eased gently over the pelvic brim of the cow. In cases such as these the device of the invention offers an important advantage over known obstetric appliances because the operator can feel any obstructions and because of the provision of independently rotatable winding drums he is able to apply different tensions to each of the forelegs of the offspring to ensure that it emerges in a correct position. In the later stages of delivery, after the offspring's eyes appear at the dam's vagina, the offspring should be pulled more quickly and evenly, and at this stage the two winding drums may be rotated in unison. In a modification of the traction means 4 a coupling device (not shown) may be provided for coupling the drums 11, 12 when it is desired to rotate them in unison. In cases where no difficulties or obstructions arise it may be possible to deliver the offspring using one winding drum only and this is particularly the case where the dam is lying on her side during calving. In this situation the device can be rested on its side on the ground and the uppermost winding drum only is rotated. In the later stages of calving when the offspring is being delivered more quickly the two delivery ropes may be wound up on the single uppermost winding drum and, if necessary, extra leverage is obtained by increasing the length of the handle 17.

Figure 5:
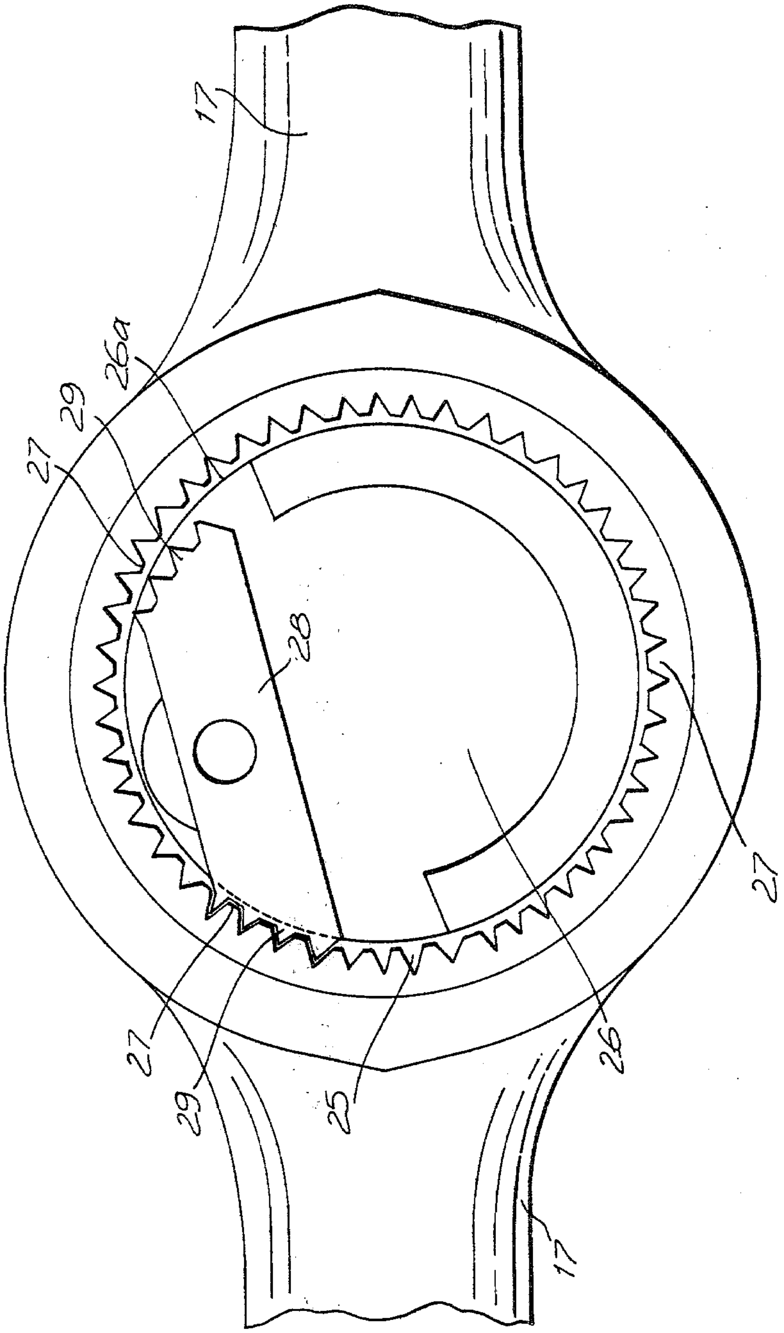
FIG. 5 shows an alternative form of non-return mechanism for use with the winding drum of FIG. 1.

In the modification of the invention shown to an enlarged scale in FIG. 5, the lock nuts 20 are replaced by a pawl and ratchet arrangement which can be used throughout the delivery procedure but which is particularly suitable for use at the later stage of delivery when the offspring is being pulled rather quickly. The pawl and ratchet arrangement prevents return-movement of the drum. In this arrangement each arm 17, for revolving the drums 11, 12, is formed with a cylindrical housing 25, which receives an end 26 of one of the axles 13, 14. The interior of the annular wall of the housing 25 is formed with ratchet teeth 27. The end 26 of the axle contains a spring-loaded pawl 28 which can be tumbled by a lever (not shown) into a position in which teeth 29 on the pawl engage with the ratchet teeth 27 to permit rotation of the winding drum in one direction only. In the other position of the pawl the teeth 29 are recessed below the bearing surface 26a of the axle and are out of engagement with the ratchet teeth 27 thus permitting the winding drum to rotate freely in either direction.

Thus, in the early stages of delivery the pawl 28 is disengaged from the ratchet teeth 27 to permit free movement of the winding drums in both directions and to enable the operator to sense and quickly react to any difficulties occurring in the delivery of the offspring. However, in the later stages of delivery when the offspring must be pulled more quickly the pawl 28 can be tumbled into the engaged position to prevent return movement of the winding drums. It will be appreciated that the pawl and ratchet arrangement described is similar to that commonly used in ratchet wrenches.

The end frame 1, longitudinal frame member 3, winding drums 11, 12 and handles 17 may be made from tubular steel and the parts welded together. Alternatively, in order to keep the device as light as possible the components may be made from aluminium or other lightweight material.

Figure 6:
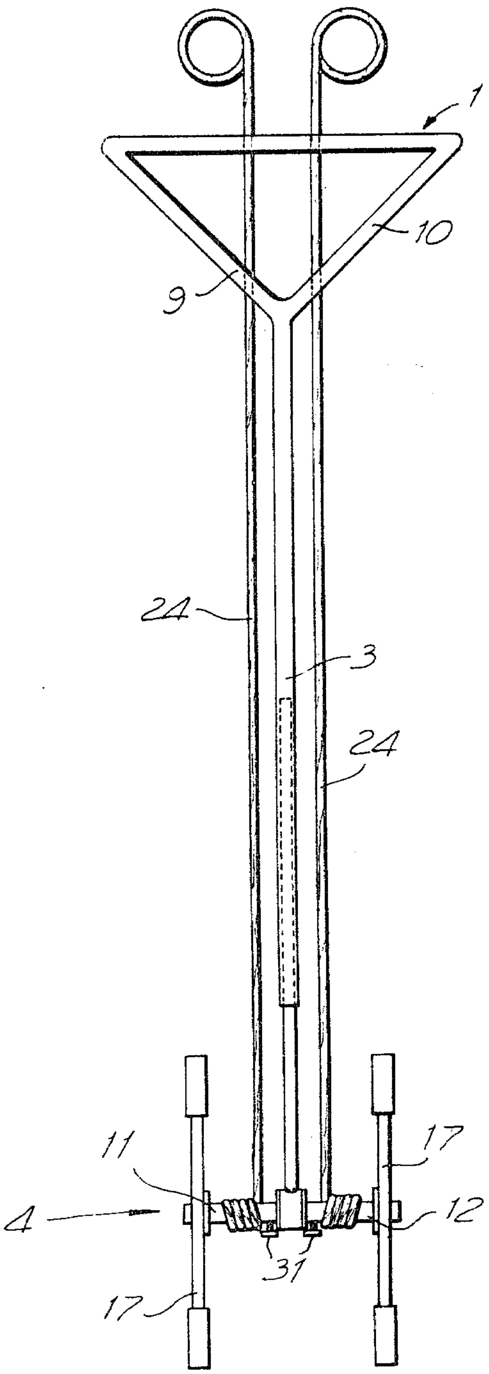
FIG. 6 is a plan view of a second embodiment of an obstetric device according to the invention.

As shown at 30 in FIG. 1, the Y-shaped longitudinal member 3 may be made from two interfitting parts to enable the device to be dismantled for carriage purposes. Alternatively, in the embodiment shown in FIG. 6, the longitudinal frame member 3 is telescopic and is adjustable in length. Furthermore, the winding drums 11, 12 are provided with brakes in the form of screws 31 threaded in bosses in the drums, and the ends of the screws may be adjusted to frictionally engage with the axles 13, 14. Apart from these modifications, the embodiment of FIG. 6 is similar to that of FIG. 1 and like parts are identified by like reference numerals.

I claim:

1. An obstetric device for assisting in the birth of animals comprising:
   (a) an end frame which is adapted to abut the pelvis of the dam and which defines an aperture through which the nascent offspring may be delivered,
   (b) a longitudinal frame member extending perpendicularly away from the end frame member and connected thereto by a substantially U-shaped portion which lies in a plane normal to the end frame, the legs of the U-shaped portion being secured to opposite side portions of the end frame at positions on said side portions below their mid-points but above their lower ends such that the greater part but not all of the delivery aperture is positioned above the longitudinal frame member,
   (c) a substantially T-shaped portion on the end of the longitudinal frame member remote from the end frame, the short arms of the T-shaped portion forming axles exending laterally outwardly from the longitudinal frame member and at right angles thereto,
   (d) a winding drum rotatably mounted on each axle and each winding drum being rotatable independently of the other,
   (e) a delivery rope secured by one end to, and adapted for winding up on, each of said winding drums, the other end of each delivery rope being provided with means for attaching the rope to the forelegs of the nascent offspring,
   (f) a handle located to each outer side of, and spaced from, the longitudinal frame member and connected to each winding drum, by means of which each drum can be manually rotated independently of each other to apply separate tension to each delivery rope, and
   (g) means permitting free movement of the winding drums in both directions.

2. An obstetric device for assisting in the birth of animals comprising:
   (a) an end frame to which is attached at least one longitudinal frame member extending rearwardly and perpendicularly away from the end frame, and in which the frame has a top portion, a bottom portion and two side portions which define an aperture through which the nascent offspring may be delivered, abutment members connected to each side portion and converging rearwardly of said end frame in the general direction of the longitudinal frame member, whereby when the device is in use the end frame is adapted to abut the pelvis of the dam with the top frame portion positioned above the tail of the dam, while at least a portion of each abutment member is adapted to engage with the ischial tuberosities of the dam, and the bottom portion of the frame is adapted to press against the legs of the dam,
   (b) a pair of winding drums rotatably mounted on an axle or axles located at the end of the longitudinal frame remote from the end frame and which extend transversely of said longitudinal frame in a plane parallel to the plane of the end frame, and each winding drum being rotatable independently of the other,
   (c) a delivery rope attached by one end to, and adapted for winding up on each of said winding drums the other end of each delivery rope being provided with means for attaching the rope to the forelegs of the nascent offspring, and
   (d) a handle located to each outer side of, and spaced from, the longitudinal frame member and connected to each winding drum, by means of which each drum can be manually rotated independently of the other to apply separate tension to each delivery rope, said at least one longitudinal frame member being connected to the end frame by means of a substantially U-shaped or V-shaped member the limbs of which form said abutment member and which define a cradle which is adapted when in use to receive the ischial tuberosities of the dam against which the abutment members are adapted to anchor, the limbs of the U-shaped or V-shaped abutment member being connected to opposite side portions of the end frame at positions below their mid-points but above their lower ends such that the greater part but not all of the delivery aperture is positioned above said abutment member.

* * * * *